US009642908B2

(12) United States Patent
Allen

(10) Patent No.: US 9,642,908 B2
(45) Date of Patent: May 9, 2017

(54) EQUINE DISEASE MODEL FOR HERPESVIRUS NEUROLOGIC DISEASE AND USES THEREOF

(75) Inventors: George P. Allen, Nicholasville, KY (US); Glenda Ross, legal representative, Nicholasville, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 13/054,608

(22) PCT Filed: Jul. 29, 2009

(86) PCT No.: PCT/US2009/004409
§ 371 (c)(1),
(2), (4) Date: Jun. 2, 2011

(87) PCT Pub. No.: WO2010/014241
PCT Pub. Date: Feb. 4, 2010

(65) Prior Publication Data
US 2011/0289606 A1    Nov. 24, 2011

(51) Int. Cl.
*A61K 38/00* (2006.01)
*A61K 39/245* (2006.01)
(Continued)

(52) U.S. Cl.
CPC ............ *A61K 39/245* (2013.01); *A61K 39/12* (2013.01); *A61K 2039/5254* (2013.01); *A61K 2039/543* (2013.01); *C12N 2710/16734* (2013.01)

(58) Field of Classification Search
None
See application file for complete search history.

(56) References Cited

U.S. PATENT DOCUMENTS 5,747,476 A    5/1998  Russell et al.
6,528,250 B1   3/2003  Montelaro et al.
(Continued)

FOREIGN PATENT DOCUMENTS

WO    WO 00/08165 A1    2/2000

OTHER PUBLICATIONS

Henninger et al. Outbreak of neurologic disease caused by equine herpesvirus-1 at a university equestrian center. J Vet Intern Med. Jan.-Feb. 2007;21(1):157-65.*

(Continued)

*Primary Examiner* — Michelle S Horning
(74) *Attorney, Agent, or Firm* — Anne M. Rosenblum

(57) ABSTRACT

Disclosed is an in vivo equine disease model and a method of preparing the disease model for equine herpesvirus-1 neurological disease comprising a horse having a low pre-exposure level of herpesvirus-specific CTL precursors wherein the horse is experimentally infected with a neuropathogenic strain of equine herpesvirus or a mutant thereof. Also disclosed is a method of quantifying the risk factors and predicting the development of clinical neurologic signs of equine herpesvirus-1 neurological disease in a horse. Also described in the invention is the determination of the risk of developing the clinical neurologic signs by a mathematical equation. A new live, attenuated vaccine formulation is disclosed that is effective against neurologic disease due to equine herpesvirus-1.

8 Claims, 4 Drawing Sheets

(51) Int. Cl.
*A61K 39/12* (2006.01)
*A61K 39/00* (2006.01)

(56) References Cited

U.S. PATENT DOCUMENTS

| | | | |
|---|---|---|---|
| 7,060,282 | B1 | 6/2006 | Sondermeijer et al. |
| 7,153,513 | B2 * | 12/2006 | Chu ............................ 424/218.1 |
| 7,226,604 | B2 | 6/2007 | Mellencamp |
| 7,323,178 | B1 | 1/2008 | Zhang et al. |
| 2005/0003342 | A1 * | 1/2005 | Davis Poynter et al. ........ 435/5 |
| 2006/0233831 | A1 * | 10/2006 | Parisot et al. ............. 424/204.1 |

OTHER PUBLICATIONS

Rosas et al. Equine herpesvirus type 1 modified live virus vaccines: quo vaditis? Expert Rev Vaccines. Feb. 2006;5(1):119-31.*

Slater et al., Report of the equine herpesvirus-1 Havemeyer Workshop. San Gimignano, Tuscany, Jun. 2004, Veterinary Immunology and Immunopathology, 2006, vol. 111, pp. 3-13.

Craigo et al., "Transient immune suppression of inapparent carriers infected with a principal neutralizing domain-deficient equine infectious anaemia virus induces neutralizing antibodies and lowers steady-state virus replication," J. of General Virology, 2002, vol. 83, pp. 1353-1359.

Goodman et al., "A Point Mutation in Herpesvirus Polymerase Determines Neuropathogenicity," PLoS Pathogens, Nov. 2007, vol. 3, pp. 1583-1592.

Cernea et al., "Evaluation of egg hatch assay for detection and risk analyses of antihelmintic resistance in strongylid nematodes of horses," Scientia Parasitologica, 2004, vol. 1-2, pp. 175-179.

Kydd et al., "The Power of Limiting Dilution Analysis," Havemeyer Foundation Minograph Series No. 4: Proceedings of a Workshop on Equine Immunology in 2001 [online], Edited by D. P. Lunn and J.F. Wade, pp. 65-66 [retrieved from Internet for International Search Report on Dec. 20, 2009 from: <http://www.havemeyerfoundation.org/PDFfiles/monograph4.pdf>.

Paillot et al., "Frequency and phenotype of EHV-1 specific, IFN-gamma synthesising lymphocytes in ponies: The effects of age, pregnancy and infection," Development and Comparative Immunology, Pergamon Press, US, vol. 31, No. 2, pp. 202-214, Jan. 1, 2007.

O'Neill et al., "Determination of equid herpesvirus 1-specific, CD8+, cytotoxic T lymphocyte precursor frequencies in ponies," Veterinary Immunology and Immunopathology, vol. 70, No. 1-2, pp. 43-54, Sep. 1, 1999.

Smith et al., "Virulence of the V592 Isolate of Equid Herpesvirus-1 in Ponies," Journal of Comparative Pathology, Academic Press, London, GB, vol. 122, No. 4, pp. 288-297, May 1, 2000.

* cited by examiner

EQUINE DISEASE MODEL FOR HERPESVIRUS NEUROLOGIC DISEASE AND USES THEREOF

CROSS-REFERENCE TO RELATED APPLICATIONS

This application commences the national stage under 35 U.S.C. §371 of PCT International Application No. PCT/US2009/004409, filed on Jul. 29, 2009, which claims the priority benefit of U.S. Provisional Application No. 61/137,412, filed on Jul. 30, 2008. The prior applications are incorporated herein by reference in their entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A "SEQUENCE LISTING"

The material on a single compact disc containing a Sequence Listing file provided in this application is incorporated by reference thereto.

BACKGROUND OF THE INVENTION

Field of the Invention

The present invention concerns quantifiable risk factors for the post-exposure development of equine herpesvirus-1 neurological disease and their use to provide a new equine experimental disease model for evaluating and developing effective vaccines for the protection of horses against equine herpesvirus-1 neurological disease. The invention further relates to a new live, attenuated vaccine and its use to prevent neurological disease caused by equine herpesvirus-1.

Description of Related Art

All patents and publications cited in this specification are hereby incorporated by reference in their entirety.

Epizootics of neurological disease caused by equine herpesvirus-1 (EHV-1) have been reported with increasing frequency in the United States during the past several years (United States Department of Agriculture, "Equine herpes virus myeloencephalopathy: A potentially emerging disease," *USDA: APHIS: Veterinary Services: Centers for Epidemiology and Animal Health, Center for Emerging Issues Information Sheet*, 2007). Characterized by high neurologic morbidity and case fatality rates, resistance to prevention by vaccination, and the ability to affect horses of all breeds and ages, EHV-1 myeloencephalopathy has the potential for causing catastrophic losses to both the welfare of horses and the economy of equine-based businesses (M. T. Donaldson and C. R. Sweeney, "Equine herpes myeloencephalopathy," *Compend Contin Edu Pract Vet* 19:864-871 (1997); W. D. Wilson, "Equine herpesvirus 1 myeloencephalopathy," *Vet Clin North Am Equine Pract* 13:53-72 (1997); R. W. Henninger et al., "Epidemic neurologic disease due to equine herpesvirus-1 at a university equestrian center," *J Vet Intern Med* 21:157-165 (2007); C. van Maanen et al., "Neurological disease associated with EHV-1 infection in a riding school: clinical and virological characteristics," *Equine Vet J* 33:191-196 (2001); M. J. Studdert et al., "Outbreak of equine herpesvirus type 1 myeloencephalitis: new insights from virus identification by PCR and the application of an EHV-1-specific antibody detection ELISA," *Vet Rec* 153:417-423 (2003); S. M. Reed and R. E. Toribio, "Equine herpesvirus 1 and 4," *Vet Clin North Am Equine Pract* 20:631-642 (2004); T. A. Jackson and J. W. Kendrick, "Paralysis of horses associated with equine herpesvirus 1 infection," *J Amer Vet Med Assoc* 158:1351-1357 (1971); K. M. Charlton et al., "Meningoencephalomyelitis in horses associated with equine herpesvirus 1 infection," *Vet Pathol* 13:59-68 (1976); P. B. Little and J. Thorsen, "Disseminated necrotizing myeloencephalitis: a herpes-associated neurological disease of horses," *Vet Pathol* 13:161-171 (1976); H. Platt et al., "Pathological observations on an outbreak of paralysis in broodmares," *Equine Vet J* 12:118-126 (1980); R. S. Greenwood and A. B. Simpson, "Clinical report of a paralytic syndrome affecting stallions, mares and foals on a Thoroughbred studfarm," *Equine Vet J* 12:113-117 (1980); K. E. Whitwell and A. S. Blunden, "Pathological findings in horses dying during an outbreak of the paralytic form of Equid herpesvirus type 1 (EHV-1) infection," *Equine Vet J* 24:13-19 (1992); C. W. Kohn and W. R. Fenner, "Equine herpes myeloencephalopathy," *Vet Clin N Am: Equine Pract* 3:405-419 (1987)).

Although the specific immune mechanisms required for control of EHV-1 neurologic disease are largely not established, a well known immunoeffector mechanism for controlling the level of cell-associated viremia of other herpesviruses is cytotoxic T lymphocytes (CTL) (A. M. Arvin, "Cell-mediated immunity to varicella-zoster virus," *J Infect Dis* 166:35-41 (1992); S. Martin et al., "Herpes simplex virus type 1 specific cytotoxic T lymphocytes recognize virus nonstructural proteins," *J Virol* 62:2265-2273 (1988)). Later investigations of Kydd et al. demonstrated that resistance to EHV-1 abortion in ponies was associated with high frequencies of pre-exposure, EHV-1 specific CTLp in the blood circulation (J. H. Kydd et al., "Pre-infection frequencies of equine herpesvirus-1 specific, cytotoxic T lymphocytes Fcorrelate with protection against abortion following experimental infection of pregnant mares," *Vet Immunol & Immunopathol* 96:207-217 (2003)). However, the Kydd et al. study dealt solely with abortion as a disease outcome of EHV-1 infection and did not address the neurological manifestation of EHV-1 infection.

Recent molecular characterization of EHV-1 isolates recovered from outbreaks of neurologic disease has revealed that the majority of isolates are variant strains of the virus that possess an adenine (A) to guanine (G) base substitution at position 2254 of the gene that encodes the viral DNA polymerase (open reading frame #30; ORF30) (J. Nugent et al., "Analysis of equine herpesvirus type 1 strain variation reveals a point mutation of the DNA polymerase strongly associated with neuropathogenic versus non-neuropathogenic disease outbreaks," *J Virol* 80:4047-4060 (2006)). It has been postulated that this unique mutation in the catalytic subunit of the viral replication complex endows such virus strains with an enhanced replicative vigor that increases the number and severity of lesions of necrotizing vasculitis in the blood vessels of the central nervous system of the infected horse (K. E. Whitwell and A. S. Blunden, "Pathological findings in horses dying during an outbreak of the paralytic form of Equid herpesvirus type 1 (EHV-1) infection," *Equine Vet J* 24:13-19 (1992); G. P. Allen and C. C. Breadthnach, "Quantification by real-time PCR of the magnitude and duration of leukocyte-associated viraemia in horses infected with neuropathogenic versus non-neuropathogenic strains of equine herpesvirus-1," *Equine Vet J* 38:252-257 (2006)).

Concern has been voiced that genetic change in the herpes viral agent with a concomitant increase in its virulence is resulting in the neurological manifestation of EHV-1 infection that is increasing in incidence, morbidity and case fatality rates (United States Department of Agriculture, "Equine herpes virus myeloencephalopathy: A potentially emerging disease," *USDA: APHIS: Veterinary Services: Centers for Epidemiology and Animal Health, Center for Emerging Issues Information Sheet*, 2007). The increase in incidence of the high-mortality herpesviral neurological disease of horses that is not protected against by currently marketed vaccines has fueled genuine concerns about its effect on the future economic prosperity of the U.S. horse industry. Of particular alarm to the equine industry is its recent targeting of horses in riding/boarding stables and of young horses assembled at race track venues for training and racing, with consequent high mortality rates and severe economic losses to the boarding and racing sectors of the industry. Although efforts to develop a more effective, second-generation vaccine against the neurologic herpesvirus disease are underway by several vaccine manufacturers, no equine disease model exists for assessing the effectiveness of such experimental vaccines.

In fact, a practical neurological disease model has never been created, either in connection with standard laboratory mice, rats or guinea pigs where the neurological effects of EHV-1 infection can never develop, or even from prior equine studies of EHV-1 in horses or ponies. Earlier challenge studies, including those reported in the published paper by T. O'Neill et al., "Determination of equid herpesvirus 1-specific, CD8+, cytotoxic T lymphocyte precursor frequencies in ponies," *Vet Immunol & Immunopathol* 70:43-54 (1999), did not address the neurological manifestation of EHV-1 infection or disease. Since the oldest group of 9-year-old ponies in that 1999 study showed frequencies of EHV-1 specific CTLp that were high before experimental infection, it was concluded by the co-authors that high CTLp frequency may correlate with immunity to EHV-1. Furthermore, the ponies never reached the point where they presented any neurological signs. Their blood analysis and physical characteristics are of limited value, consequently, in determining the factors giving rise to neurological disease, the traits of a neurological disease model or the criteria useful in predicting development of neurological disease.

Previously, vaccination strategies have focused on the well-known murine model of EHV-1 infection in which the efficacy and safety of the EHV-1 vaccines are initially tested in vivo in mice rather than directly in horses (see, for example, A. R. Frampton et al., "Meningoencephalitis in mice infected with an equine herpesvirus 1 strain KyA recombinant expressing glycoprotein I and glycoprotein E," *Virus genes* 29(1):9-17 (August 2004); C. F. Colle et al., "Equine herpesvirus-1 strain KyA, a candidate vaccine strain, reduces viral titers in mice challenged with a pathogenic strain, RacL," *Virus Research* 43(2):111-124 (August 1996); T. Kondo et al., "A protective effect of epidermal powder immunization in a mouse model of equine herpesvirus-1 infection," *Virology* 318(1):414-419 (January 2004); C. Walker et al., "Comparison of the pathogenesis of acute equine herpesvirus 1 (EHV-1) infection in the horse and the mouse model: a review," *Veterinary Microbiology* 68(1):3-13 (August 1999); K. M. Ruitenberg et al., "DNA-mediated immunization with glycoprotein D of equine herpesvirus 1 (EHV-1) in a murine model of EHV-1 respiratory infection" *Vaccine* 17(3): 237-244 (February 1999); P. A. M. van Woensel et al., "A mouse model for testing the pathogenicity of equine herpes virus-1 strains," *Journal of Virological Methods* 54(1):39-49 (July 1995); M. K. Baxi et al., "Molecular studies of the acute infection, latency and reactivation of equine herpesvirus-1 (EHV-1) in the mouse model," *Virus Research* 40(1):33-45 (January 1996).

While the murine model has served its purpose as a model for simple EHV-1 infections characterized by clinical signs such as pyrexia (abnormally elevated body temperature) or loss of body weight, the mouse as an experimental model for studying the neurological disease and efficacious vaccine candidates in large horses has several drawbacks. First of all, the EHV-1 infection in the mouse never can progress to express the same breadth of neurological signs that plague the natural host, namely, horses, thus failing to provide a complete picture as a viral vaccine candidate model to permit adequate vaccination strategies in horses. For instance, myeloencephalopathic disease like that exhibited by herpesvirus infected horses does not develop in the experimental mouse model of herpesvirus disease. Secondly, a major adverse effect of infection in pregnant mares is the induction of spontaneous infectious abortions, which cannot be duplicated or investigated in the vaccination studies run in the classic murine model. Thirdly, without a solid understanding of the clinical signs and progression of the EHV-1 disease in horses, the vaccine candidates will not have broad applicability and activity to prevent more serious neurologic signs than simple infections caused by the single etiological agent in the mouse. More research on the progression of the disease in the natural host is necessary beyond the bare minimal effects from infection in the mouse. Fourthly, the detection of new mutant equine herpesviruses has further limited the application of the murine model as a practical animal model for vaccine purposes.

Eventually, final testing of the safety and efficacy of the virus strains will take place in vivo in horses. Equine vaccines, which are commercially available and described in the art, are subsequently tested on horses, but typically only after the initial efficacy and safety studies in the classic murine model that leave a wide gap in vaccination data. For a case directly on point, the horse vaccines comprising a mutant EHV-1 or EHV-4 virus disclosed in U.S. Pat. No. 7,060,282 are shown as being conventionally tested first through in vivo studies in laboratory mice. The patentees note the limitations of using the standard murine model to confirm protective activity in horses. They indicate that while pathogenicity of individual EHV-1 strains can be correlated from the mouse model to the behavior in the natural equine host, more conclusive proof is obtained only from vaccination trials in horses. Patentees further complain that the level of protection against challenge infection and ultimately in preventing abortion in pregnant mares can only be established in the target animal and, thus, the initial murine testing is of limited value in the final analysis.

There is a definite art-recognized problem with the classic mouse model that the present invention solves by developing the first equine disease model for the successful reproduction of herpesvirus-1 neurological disease in the horse.

It is therefore an important object of the present invention to provide a unique equine experimental disease model that is useful for evaluating and developing safe and effective vaccines in the protection of horses against equine herpesvirus infections and, more specifically, against equine herpesvirus-1 neurological disease.

It is a further important object of the present invention to identify the parameters in equine herpesvirus inoculated horses that are highly correlated with post-inoculation development of clinical disease and particularly to find the quantifiable risk factors that are directly associated with the development of clinical neurological signs in horses exposed to equine herpesvirus-1.

It is another important object of the invention to find an effective modified live, virus vaccine that protects horses against neurological disease due to infection caused by equine herpesvirus-1. While presently known EHV-1 vaccines that claim protection against neurologic disease as well as respiratory disease and abortion are largely based on inactivated viruses (see, for example, U.S. Pat. Nos. 7,323,178 and 7,226,604), it is art-recognized that live and attenuated viral vaccines, as a general rule, can induce a better immune response. Therefore, this goal of the present invention is to provide a new and improved live, attenuated vaccine formulation that stimulates a protective immune response against neurologic disease due to equine herpesvirus-1.

Further purposes and objects of the present invention will appear as the specification proceeds.

The foregoing objects are accomplished by providing a novel equine disease model, the determination of the quantifiable risk factors for the post-exposure development of equine herpesvirus-1 neurological disease and a unique equine herpesvirus-1 vaccine as described herein.

BRIEF SUMMARY OF THE INVENTION

The present invention relates to a new disease model for equine herpesvirus-1 neurological disease comprising a horse possessing the following quantifiable risk factors that highly correlate with the post-exposure development of equine herpesvirus-1 neurological disease: (1) the magnitude of post-infection, systemically circulating EHV-1 infected leukocytes (viremic load); (2) the pre-exposure frequency of circulating cytotoxic T lymphocyte precursors (CTLp) specific for EHV-1; (3) the ORF30-2254 genotype of the infecting strain of EHV-1; and (4) age category of the exposed horse. Also embraced by the present invention is the previously unknown identification of these risk factors that directly correlate to the development of clinical signs of neurological disease in horses exposed to equine herpesvirus-1 and making novel use of such identification in a new method of quantifying the risk factors and predicting the development of clinical neurologic signs of equine herpesvirus-1 neurological disease. Of the identified risk factors, infection by an ORF30 $G_{2254}$ strain of EHV-1 has the strongest association with the probability of clinical progression of the herpesviral infection to clinically overt neurological disease. Important embodiments of the invention are thus drawn to the in vivo equine disease models wherein the horse is experimentally infected, typically through intranasal administration, with a neuropathogenic strain of equine herpesvirus or a mutant thereof, such as the ORF30 $G_{2254}$ strain of EHV-1, in which the horse has a low pre-exposure level of herpesvirus-specific CTL precursors and/or is about 20 years of age or older as well as the method of preparing the in vivo equine disease model for EHV-1 neurological disease. An additional embodiment of the invention employs a live, attenuated strain of equine herpesvirus or a mutant thereof as the antigen in a modified vaccine and its use to protect horses against neurological disease due to infection caused by equine herpesvirus-1.

BRIEF DESCRIPTION OF THE DRAWINGS

The background of the invention and its departure from the art will be further described herein below with reference to the accompanying drawings, wherein.

DETAILED DESCRIPTION OF THE INVENTION

Figure 1:
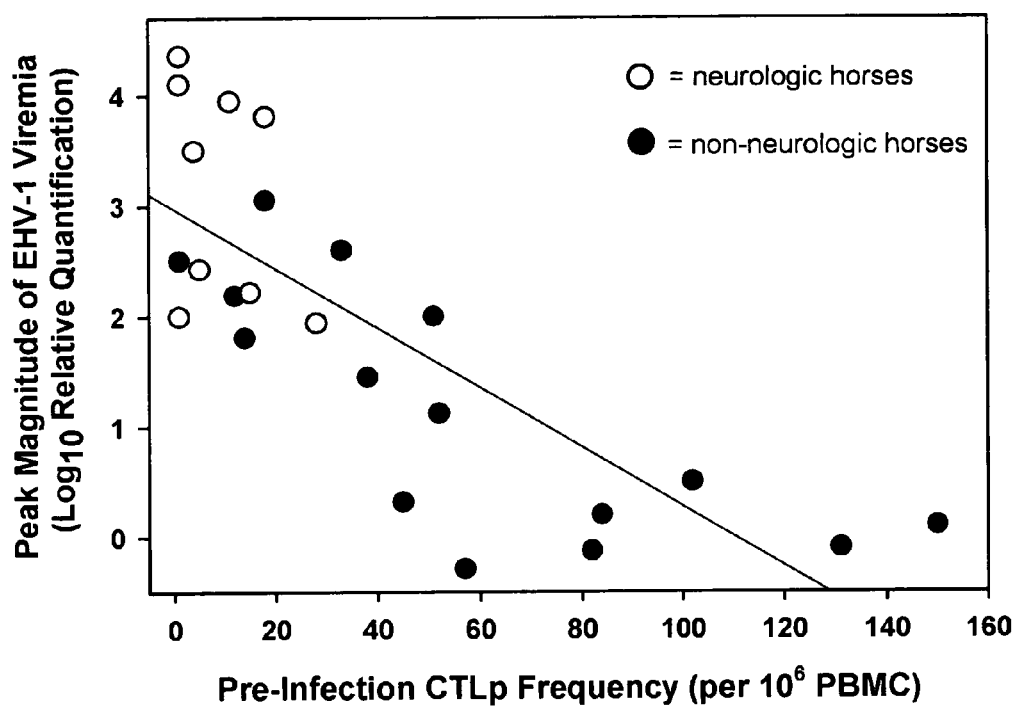
FIG. 1 illustrates the relationships among peak magnitude of viremia, pre-infection CTLp frequency and development of clinical neurologic disease in 24 horses following exposure to neuropathogenic EHV-1. White circles represent horses with neurologic signs while the black circles stand for the horses without neurologic signs. EHV-1 DNA present in equine peripheral blood mononuclear cells (PBMC) was quantified by real-time qPCR and the amount expressed as $\log_{10}$ of the fold-difference relative to that present in a reference calibrator PBMC DNA (relative quantification; RQ). Determination in equine PBMC of the frequency of CTL precursors (CTLp) specific for EHV-1 was done by limiting dilution analysis.
Figure 2:
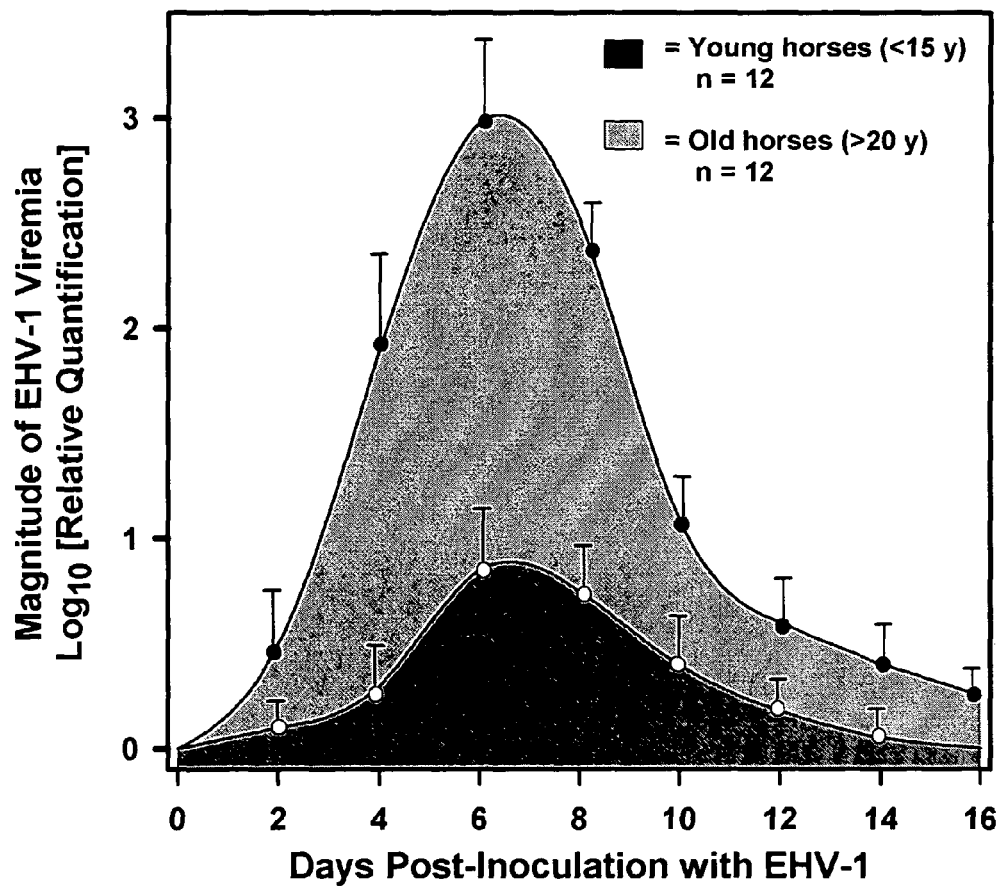
FIG. 2 shows the mean±SE daily values for magnitude of leukocyte-associated (PBMC-associated) viremia in 12 young (<15 years, shown by darkly shaded area) and 12 old (>20 years, shown by lightly shaded area) horses following intranasal inoculation with a neuropathogenic strain of EHV-1. EHV-1 DNA present in equine peripheral blood mononuclear cells (PBMC) was quantified by real-time qPCR and the amount expressed as the fold-difference relative to that present in a reference calibrator PBMC DNA (relative quantification; RQ). The results are presented as an "area-fill plot" to visually illustrate the two-dimensional character (magnitude and duration) of EHV-1 viremia, in which the total viral load experienced by the infected horse is proportional to the shaded area beneath each curve. Standard errors of the mean RQ values for each age group of 12 horses on each sampling day post-inoculation are indicated by the error bars. The differences between the two age groups of mares in their mean magnitude of EHV-1 viremia are significant at P=≤0.05 for post-inoculation days 4 through 10.
Figure 3:
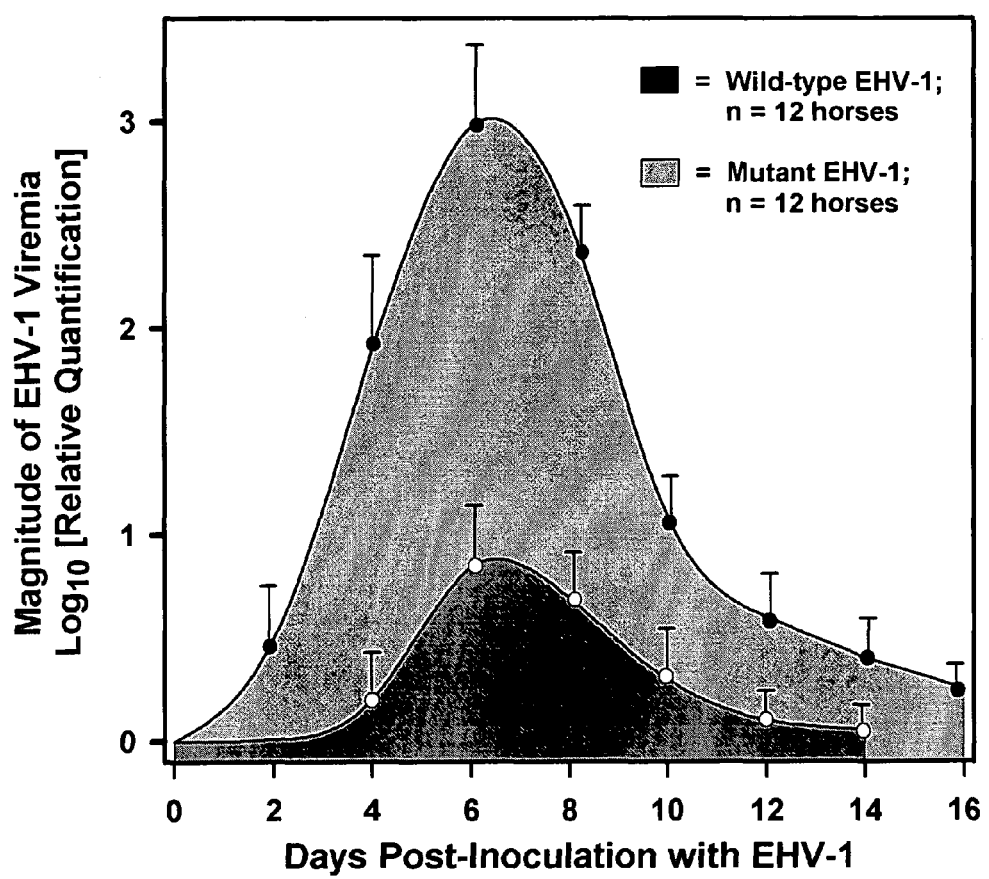
FIG. 3 shows a comparison of the mean±SE daily magnitude of leukocyte-associated (PBMC-associated) viremia in 24 elderly horses (>20 years) following inoculation with either an ORF30 $A_{2254}$ strain (T262, the wild-type EHV-1 strain shown by darkly shaded area; n=12 horses) or an ORF30 $G_{2254}$ strain (T953, the mutant EHV-1 strain shown by lightly shaded area; n=12 horses) of EHV-1. EHV-1 DNA present in equine peripheral blood mononuclear cells (PBMC) was quantified by real-time qPCR, and the amount was expressed as $\log_{10}$ of the fold-difference relative to that present in a reference calibrator PBMC DNA (relative quantification; RQ). The results are presented as an "area-fill plot" to visually illustrate the two-dimensional character (magnitude and duration) of EHV-1 viremia, in which the total viral load inflicted upon the infected horse is proportional to the shaded area beneath each curve. Standard errors of the mean $\log_{10}$ RQ values for each treatment group of 12 horses are indicated by the error bars. The differences in the mean magnitude of EHV-1 viremia resulting from inoculation with the two genetic strains of EHV-1 are significant at P=≤0.05 for post-inoculation days 4 through 12.

In accord with the present invention, there is provided a unique equine experimental disease model of equine herpesvirus-1 (hereinafter referred to as "EHV-1") infection and neurological disease, that is highly useful for the evaluation and the development of safe and efficacious vaccines for the protection of horses against debilitating neurological disease. The innovative neurological disease model of EHV-1 is defined and the disease is reproduced in horses for the first time. Understanding the pathogenesis in horses and quantifying the risk factors for the post-exposure incidence of EHV-1 disease permit the valuable development of vaccine strategies that can target the specific signs of disease. As a result of this invention, it is now possible to considerably improve and to preferentially target the mode of action of EHV-1 vaccine candidates to obtain a more reproducible and reliable outcome than previously achievable.

An important embodiment of this invention encompasses the particular in vivo equine disease model in which an experimental horse having a low pre-exposure level of herpesvirus-specific CTL precursors and/or is about 20 years of age or older is challenged with a neuropathogenic strain of equine herpesvirus or a mutant thereof. Distinguishing from natural infections, the horse of the present invention is inoculated (i.e., artificially infected) by a person who gives an effective challenge dose to the horse, typically by intranasal administration of EHV-1 although other standard routes of administering the viral agent such as intrarectal, oral, intramuscular, intradermal, subcutaneous and the like are possible. The amount of an effective challenge dose, which is the quantity of EHV-1 sufficient to cause signs of infection, can be readily determined and titrated through routine testing in horses. The neuropathogenic strain of EHV-1 or the mutant thereof includes, but is not limited to, the ORF30 $G_{2254}$ strain of EHV-1 such as T953, Army 183, Ab4, etc. and others known to those of ordinary skill in the veterinary viral art. Preferably, the experimental disease model has been created by intranasal inoculation with an effective challenge dose of the neuropathogenic ORF30 $G_{2254}$ strain of EHV-1 and the horse possesses high levels of post-infection, leukocyte-associated viremia. Of particular benefit as a highly desirable experimental model of this invention is the in vivo equine disease model for EHV-1 neurological disease that develops or presents with clinical signs of myeloencephalopathy.

Another important embodiment of the present invention relates to the method of preparing the in vivo equine disease model for EHV-1 neurological disease which comprises obtaining a horse that possesses low pre-infection levels of EHV-1 specific CTL precursors and/or is roughly 20 years of age or older and inoculating the horse intranasally with an effective challenge dose of a neuropathogenic strain of EHV-1, preferably the ORF30 $G_{2254}$ strain of EHV-1 such as, for example, the T953, Army 183, Ab4 strains of EHV-1, etc.

Commercial vaccine developers can use the reproducible, neurologic disease model for equine herpesvirus myeloencephalopathy for assessment of the protective efficacy of their candidate antiviral vaccines against the herpesviral neurological disease of horses. The innovativeness of the invention is found in the discovery of the quantifiable risk factors that permit the selection of the experimental horse subjects and the challenge strain of herpesvirus that allow reproduction of the neurological disease in a high proportion of virus-inoculated horses. In view of this discovery, the present invention further embraces a new method of quantifying risk factors and predicting the development of clinical neurologic signs of equine herpesvirus-1 neurological disease in a horse. The unique method comprises the two steps of: (a) determining the pre-infection CTLp frequency to be less than approximately 40 EHV-1 specific CTLp per $10^6$ (i.e., per million) PBMC (equine peripheral blood mononuclear cells) and/or determining the age of the horse to be approximately 20 years of age or older; and (b) determining the post-infection viremic load following exposure to EHV-1 to be approximately 10-fold or more over the viremic load present in horses following exposure to a non-neuropathogenic strain of EHV-1. Desirably, step (a) embraces determining the pre-infection CTLp frequency to be less than approximately 20 EHV-1 specific CTLp per $10^6$ PBMC and, more desirably, determining the pre-infection CTLp frequency to be less than approximately 10 EHV-1 specific CTLp per $10^6$ PBMC while step (b) independently encompasses determining the post-infection viremic load following exposure to EHV-1 to be approximately 100-fold or more greater than the viremic load present in horses following exposure to a non-neuropathogenic strain of EHV-1 and, even more desirably, determining the post-infection viremic load following exposure to EHV-1 to be greater than 1000-fold higher than the viremic load present in horses following exposure to a non-neuropathogenic strain of EHV-1.

Up until the present invention, the risk factors associated with EHV-1-induced myeloencephalopathy in horses had not yet been fully investigated. In addition, certain researchers provided incorrect conclusions regarding the factors giving rise to EHV-1 disease, which clouded the animal health issues. This invention represents a real advancement in the veterinary arts since the parameters in EHV-1 inoculated horses that are highly correlated with post-inoculation presentation of clinical neurological disease are now fully identified.

Although the underlying basis for predicting which horses will make effective experimental subjects is seen to be the magnitude of CTLp circulating in the blood, it is also now unexpectedly found that the aged horses coincidentally but almost uniformly exhibit low levels of CTLp as a result of the waning immune system that accompanies aging. Consequently, the invention also includes the bare determination of the horse age, in particular, about 20 years old or more, as a valid and sole criterion for predicting and selecting experimental subjects for the disease model.

Insofar as the age of the horse disease model is concerned, the present invention further embraces the use of foals, typically as young as roughly one week old to just about one year old in age, in which low pre-infection levels of EHV-1 specific CTL precursors are created and induced by suitable immune-suppressing agents. While a horse of any age can be immune-suppressed, the foal, which does not yet exhibit low levels of CTLp naturally, can be immunosuppressed desirably with conventional immunosuppressing drugs to impair the CTL function. The immune-suppressing agents useful in the present invention include, but are not limited to, antimetabolites such as azathioprine, mycophenolate mofetil, etc.; corticosteroids; calcineurin inhibitors such as cyclosporine, tacrolimus, etc.; sirolimus; polyclonal antibody therapy; monoclonal antibody therapy using, for example, OKT3 or daclizumab and basiliximab; and the like. Preferably, the immunosuppression is produced by dexamethasone or another comparable corticosteroid.

Inducing immunosuppression can be achieved by any standard technique known in the art (see, e.g., N. R. Barshes et al., "Pharmacologic Immunosuppression," *Frontiers in Bioscience* 9:411-420 (Jan. 1, 2004); T. J. Cutler et al., "Immunosuppression against *Sarcocystis neurona* in normal and dexamethasone-treated horses challenged with *S. neurona* sporocysts," *Veterinary Parasitology* 95:197-210 (2001); D. B. Tumas et al., "Corticosteroid immunosuppression and monoclonal antibody-mediated CD5+T lymphocyte depletion in normal and equine infectious anaemia virus-carrier horses," *J Gen Virology* 75:959-968 (1994)) By way of an example relevant to the present invention, a foal less than one year old in age is injected intravenously with 1 mg/kg of dexamethasone per body weight per day for approximately nine days to induce immunosuppression where the CTL function becomes impaired. About four to five days after treatment with dexamethasone is completed, the young horse possessing the impaired CTL function is then challenged with a suitable infecting amount of a neuropathogenic strain of EHV-1 strain to create the disease model of this invention.

Demonstration of characteristics whose quantitative levels are so highly correlated with development of post-infection EHV-1 neurological disease in the horse would be useful to the veterinary industry in the identification of practical targets for the action of future EHV-1 vaccines and antiviral drugs. As such, the primary goal met by the present invention is the recognition of parameters that are statistically associated with development of post-exposure, EHV-1 neurological disease; i.e., to identify disease risk factors in EHV-1 inoculated horses that are highly correlated with post-inoculation development of clinical neurologic disease. Identification of such neurologic risk-associated parameters gives definitive and quantifiable prognostic indicators for development of clinical EHV-1 myeloencephalopathy following infection by the herpesvirus.

A secondary goal satisfied by the current invention is the clarification of the immunological mechanisms that horses use for controlling the magnitude of EHV-1 cell-associated viremia and its vasculitis-mediated sequelae of ischemic damage to the equine central nervous system (CNS). The latter information provides valuable insight into the types of immunologic effector responses required to be elicited by vaccines for successful immunoprevention of EHV-1 paralytic disease and serves as reliable, in vitro immune correlates of vaccine protection against the neurologic disease.

As a further aspect of the present invention, it has been observed that the risk of developing the clinical neurologic signs is determined according to an equation y=a+bx wherein y is the peak viremic load, a=2.97, b=−0.027 and the variable x is the pre-infection CTLp frequency. By this equation, a linear relationship or a correlation coefficient statistic r between the two numerical variables of y and x is −0.79 is indicative of the risk of developing the clinical neurologic signs.

Illustrated in depth in the below examples, thirty-six adult, mixed breed, horse mares are inoculated intranasally with live, virulent strains of EHV-1. Blood samples, which are collected daily from the thirty-six experimental horses before and after challenge inoculation with either non-neuropathogenic (ORF30 $A_{2254}$) or neuropathogenic (ORF30 $G_{2254}$) strains of EHV-1, are analyzed for quantitative levels of leukocyte-associated viremia (measured by real-time qPCR), serum neutralizing antibody (SNA; measured by micro-neutralization test), and EHV-1-specific cytotoxic T lymphocyte precursors (CTLp; measured by limiting dilution analysis of chromium-51 release assay results). The data are examined for statistically significant associations between values of the measured parameters and the occurrence of post-challenge clinical neurologic disease in the experimentally infected horses. Correlations between age-category or breed of the EHV-1 inoculated horses and post-exposure development of neurologic disease are also examined.

The results of the challenge studies show that nine of the thirty-six EHV-1 inoculated horses develop clinical signs of central nervous system disease (ataxia, hindlimb paresis or paralysis, bladder atony, and/or recumbency). Post-exposure development of clinically apparent neurologic deficits in the study horses is positively correlated with infection by a neuropathogenic strain of EHV-1, advanced age (>20 years), elevated post-exposure viremic load, and a low pre-exposure level of virus-specific CTLp. Unexpectedly, the pre-infection serum neutralizing antibody titer has the least correlation to development of disease after exposure to EHV-1. In addition, no significant correlation is observed between horse breed and the post-infection development of neurologic signs.

Also surprising is the finding that the category of horse at greatest risk for development of myeloencephalopathy following infection by EHV-1 is the elderly horse (>20 years) exposed to a neuropathogenic strain of the virus (ORF30 $G_{2254}$) and possessing low pre-infection levels of EHV-1 specific CTL precursors and high levels of post-infection, leukocyte-associated viremia. By contrast, horses possessing high levels of pre-existing, EHV-1 specific CTL precursors, regardless of age, strain of virus, or SNA titer, are more likely to control the magnitude of post-infection, leukocyte-associated viremia and the subsequent development of EHV-1 neurologic disease. These observations serve to identify CTLp as one of the critical immune requirements for protective immunity to EHV-1 induced myeloencephalopathy. The importance of achieving high levels of vaccine induced CTL immunity in groups of horses at high risk for exposure to neuropathogenic strains of EHV-1 is clearly indicated from the results of these studies.

The results establish a strong association (P=<0.01 by Fisher's exact test) between the ORF30 genotype ($A_{2254}$ or $G_{2254}$) of the infecting strain of EHV-1 and the subsequent risk for development of clinically apparent neurologic deficits in the infected horse. While none of 12 mares inoculated with an ORF30 $A_{2254}$ EHV-1 strain exhibit neurologic signs, 8 of 12 age- and gender-matched horses inoculated with an ORF30 $G_{2254}$ strain of EHV-1 develop severe neurologic complications, with euthanasia required in 6 of the 8 neurologically affected animals. Of the several potential risk factors evaluated in this study, infection by an ORF30 $G_{2254}$ strain of EHV-1 is found to be most strongly associated with the probability of clinical progression of the viral infection to clinically overt neurological disease.

The data also establish a strong association (P=0.009 by Fisher's exact test) of the clinical progression of EHV-1 infection to neurological disease with the age-category of the inoculated horse. The risk for development of EHV-1 paralytic disease following exposure to a neuropathogenic genotype of the virus was 8-fold greater in elderly horses (>20 years) than in young to middle age adult horses (<15 years). Comparison of the post-inoculation viremic load of EHV-1 infected leukocytes present in the 12 elderly and 12 young experimental horses revealed that the mean, peak magnitude of cell-associated viremia was 100-fold greater in the elderly horse group. Thus, the quantitative load of circulating virus that follows infection by EHV-1 was defined as a major risk factor (P=<0.001 by analysis of variance test) for post-exposure development of EHV-1 CNS disease. The relatively greater susceptibility of elderly horses for development of EHV-1 neurological disease provides an experimental, neurologic disease model which may prove useful for assessment of vaccine efficacy against EHV-1 myeloencephalopathy.

To investigate the role of memory CTL specific for neuropathogenic strains of EHV-1 as effectors for reducing the magnitude of post-infection viremia, quantitative estimates of the pre-exposure frequency of EHV-1 specific CTL precursors (CTLp) in the experimental horses are determined herein below by limiting dilution analysis of Cr-51 release assays. The results in connection with the present invention identify pre-exposure frequency of EHV-1 specific CTLp as a strong correlate (regression correlation coefficient=−0.71) of the post-infection magnitude of cell-associated viremia and also as a statistically significant (P=<0.01 by logistic regression analysis) correlate of protective immunity against the myeloencephalopathy caused by infection of horses with neuropathogenic strains of EHV-1. These findings suggest a role of CTL immune responses of the horse in maintaining immunological control of EHV-1 viremia. Such results support the view that a critical-mass reservoir of circulating memory CTL, in place at the moment and location of virus exposure and capable of being activated into functional CTL with specific cytolytic activity against EHV-1, is required for controlling EHV-1 neurological disease. In order to achieve protective efficacy against EHV-1 myeloencephalopathy by vaccination, it follows that the vaccines must be able to drive the equine immune response toward the production of such cytolytically functional, effector CTL.

On the other hand, it is now discovered that the level of antibodies present prior to virus inoculation surprisingly does not correlate with protection against challenge with neuropathogenic EHV-1. After performing measurements of EHV-1 specific SNA present in the experimental horses at the time of virus inoculation, the results failed to reveal any significant relationship between pre-exposure SNA titer and the magnitude of post-infection viremia. The intracellular location of EHV-1 during most of its infection cycle within the horse may limit the effectiveness of virus neutralizing antibody in controlling the level of cell-associated EHV-1 viremia.

In sum, of the six neurologic risks evaluated for relation to the presentation of the disease entity caused by EHV-1 ((1) the magnitude of post-infection, systemically circulating EHV-1 infected leukocytes (viremic load); (2) the pre-exposure frequency of circulating cytotoxic T lymphocyte precursors (CTLp) specific for EHV-1; (3) the pre-infection titer of serum neutralizing antibody to EHV-1; (4) the ORF30-2254 genotype of the infecting strain of EHV-1; (5) breed of horse; and (6) age category of the exposed horse), it is determined that the pre-infection titer of serum neutralizing antibody to EHV-1 and the breed of horse have no correlation of the progression of EHV-1 infection to neurological disease. Surprisingly, infection by an ORF30 $G_{2254}$ strain of EHV-1 is determined to be most strongly connected to the probability of progression of the viral infection to clinically overt neurological disease.

A practical advantage of the present invention is found in the novel use of the experimental horse model to evaluate the efficacy of broad-spectrum candidate vaccines for the protection of horses against EHV-1 that not only protects against viral infection but also protects against the debilitating and often fatal EHV-1 myeloencephalopathy. A disturbing characteristic of the emerging hypervirulent, neuropathogenic mutants of equine herpesvirus-1 is their inability to be curtailed by the level or type of immunity engendered by current-generation vaccines for EHV-1. The development of second-generation vaccines against the mutant herpesvirus requires an equine neurologic disease vaccination-challenge model in which candidate vaccines can be tested for protective efficacy against EHV-1 myeloencephalopathy. The real benefit of the present invention can be readily seen in the development and validation of the unique EHV-1 neurologic disease model in horses for practical use in vaccination-challenge studies for the evaluation of the neurologic protective efficacy of candidate vaccines.

Quantitative parameters (e.g., viral genotype, age, and levels of viremia and antiviral cellular immunity (CTLp)) in EHV-1 inoculated horses, that are highly correlated with post-inoculation development of neurologic disease and identified herein, serve to define the composition of the experimental disease model of the present invention. Contributing to the high rate of experimentally produced EHV-1 neurologic disease in virus-challenged horses are the use of (1) horses with low levels of antiviral cellular immunity as subjects for vaccination and challenge, and (2) a particularly neuropathogenic challenge strain of EHV-1 (a Findlay 2003 isolate that was originally obtained from an outbreak of EHV-1 disease among 135 horses stabled at the University of Findlay Equestrian Center, Findlay, Ohio and subsequently described in R. W. Henninger et al., "Epidemic neurologic disease due to equine herpesvirus-1 at a university equestrian center," *J Vet Intern Med* 21:157-165 (2007)). The presently developed EHV-1 neurologic disease model is evaluated by studies that determine a significant level of immune protection against EHV-1 neurologic disease is unexpectedly established in horses by vaccination with a live, non-neuropathogenic strain of EHV-1.

A further important embodiment of the present invention is drawn to novel live, attenuated viral vaccines containing a non-neuropathogenic strain of EHV-1 having the ORF30 $A_{2254}$ genotype, for example, the T262 strain or a neuropathogenic strain of EHV-1 having the ORF30 $G_{2254}$ genotype such as the T953, Army 183 or Ab4 strain, as the viral antigen alone or in combination with one or more other antigens and a method of administering the vaccine to prevent or to minimize the effects of viral infection that can progress to neurologic disease as well as to protect against development of neurologic disease including myeloencephalopathy caused by the neuropathogenic viruses.

Advantageously, the new method protects horses in need of protection against neurologic disease due to neuropathogenic EHV-1 by administering to the horse an immunologically effective amount of the vaccine according to the invention. The immunologically effective amount or the immunogenic amount that inoculates the horse can be easily determined or readily titrated by routine testing. An effective amount is one in which a sufficient immunological response to the vaccine is attained to protect the horse exposed to the EHV-1 virus which causes neurologic disease and myeloencephalopathy. Preferably, the horse is protected to an extent in which one to all of the adverse physiological signs or effects of the neurologic viral disease are significantly reduced, ameliorated or totally prevented.

The foal's immunization schedule often begins at the age of about three to about six months of age. The vaccine can be administered in a single dose or in repeated doses by administering a second booster injection approximately four to six weeks after the primary immunization and then optionally giving a third booster injection another month later. Thereafter, the vaccine can be given every three months or annually depending on formulation and route of administration. Concentration of the virus in the vaccine may range, for example, from about 4 logs to about 9 logs $TCID_{50}$/dose and a reasonable dosage may be given to the horse in the amount of about 6 to about 7 logs $TCID_{50}$/dose, but should not contain an amount of virus-based antigen sufficient to result in an adverse reaction or physiological signs of viral infection. Methods are known in the art for determining or titrating suitable dosages of active antigenic agent based on the weight of the horse, concentration of the antigen and other typical factors.

The vaccine of the invention can conveniently be administered orally, intranasally, intramuscularly, intrarectally, transdermally (i.e., applied on or at the skin surface for systemic absorption) or intradermally (i.e., injected or otherwise placed under the skin). Desirably, the routes of administration are the oral, intranasal and intramuscular routes. However, the oral and intranasal routes of administration are most preferred for inducement of strong local as well as systemic immune responses.

When administered as a liquid, the present vaccine may be prepared in the form of an aqueous solution, syrup, an elixir, a tincture and the like. Such formulations are known in the art and are typically prepared by dissolution of the antigen and other typical additives in the appropriate carrier or solvent systems. Suitable carriers or solvents include, but are not limited to, water, saline, ethanol, ethylene glycol, glycerol, etc. Optional additives are, for example, certified dyes, flavors, sweeteners and antimicrobial preservatives such as antibiotics or thimerosal (sodium ethylmercurithiosalicylate) where permitted by law. Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions that contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Parenteral formulations designed for intramuscular injection and the like require proper isotonicity and pH buffering to the level of equine body fluids and tissues. Isotonicity can be appropriately adjusted with sodium chloride and other salts as needed. Suitable solvents, such as ethanol or propylene glycol, can be used to increase the solubility of the ingredients in the formulation and the stability of the liquid preparation. Further additives that can be employed in the present vaccine include, but are not limited to, dextrose, conventional antioxidants and conventional chelating agents such as ethylenediamine tetraacetic acid (EDTA). Parenteral dosage forms must be sterilized prior to use.

An adjuvant, which may be administered in conjunction with the vaccine of the present invention, is a substance that increases the immunological response of the horse to the vaccine. Since the strain of EHV-1 will be administered as a live vaccine, an adjuvant is not necessarily required in all formulations for achieving effective immunity. If it is desirable to include an adjuvant, for example, in a formulation designed for the intramuscular route of administration, the adjuvant may be administered at the same time and at the same site as the vaccine, or at a different time as a booster. Adjuvants also may advantageously be administered to the horse in a mariner or at a site different from the manner or site in which the vaccine is administered. Suitable adjuvants include, but are not limited to, metabolizable oils of plant or animal origin such as squalene (2,6,10,15,19,23-hexamethyl-2,6,10,14,18,22-tetracosahexaene) or preferably, squalane (2,6,10,15,19,23-hexamethyl-tetracosane), non-ionic block polymers or block copolymers based on ethylene oxide and propylene oxide, for example, polyoxypropylene-polyoxyethylene block copolymers (also known as (poly (ethylene oxide)-block-poly(propylene oxide)-block-poly (ethylene oxide) or Poloxamer block copolymers NF) such as Pluronic® (commercially available from BASF Corporation, Mount Olive, N.J.), saponin such as Quil A (commercial name of a purified form of *Quillaja saponaria*, available from Iscotec AB, Sweden and Superfos Biosector a/s, Vedbaek, Denmark), ethylene/maleic copolymers such as EMA-31® (a linear ethylene/maleic anhydride copolymer having approximately equal amounts of ethylene and maleic anhydride, having an estimated average molecular weight of about 75,000 to 100,000, commercially available from Monsanto Co., St. Louis, Mo.), acrylic acid copolymers, acrylic acid copolymer emulsions such as Neocryl® (an uncoalesced aqueous acrylic acid copolymer of acrylic acid and methacrylic acid mixed with styrene, commercially available from Polyvinyl Chemicals, Inc., Wilmington, Mass.), mineral oil emulsions such as MVP® (an oil-in-water emulsion of light mineral oil, commercially available from Modern Veterinary Products, Omaha, Nebr.) or mixtures thereof and the like. Other suitable adjuvants include, for example, aluminum hydroxide (alum), immunostimulating complexes (ISCOMS), cytokines (like IL-1, IL-2, IL-7, IL-12, IFN-α, IFN-β, IFN-γ, etc.), monophosphoryl lipid A (MLA), muramyl dipeptides (MDP), aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde to make the corresponding toxoid. A particularly preferred adjuvant for use in the intramuscular formulations of the invention is the unique adjuvant Metastim® (a registered trademark of Wyeth, Madison, N.J. comprising squalane and Pluronic® L-121).

The equine vaccine of the invention may remain univalent or be made multivalent and contain one or more additional antigens to promote broad spectrum immunological activity. The multivalent vaccine may include, but is not limited to, other equine viruses such as, for example, killed EHV-4, killed or live EHV-5, killed or live Equine Influenza Virus, killed Eastern, Western, and Venezuelan Encephalomyelitis viruses, inactivated West Nile Virus, or recombinant proteins or recombinant vectors expressing proteins from these viruses such as live canarypox vectors, live African Horse Sickness virus or recombinant vectors expressing the African Horse Sickness virus antigens, and the like. In addition, the multivalent vaccine may include, but is not limited to, bacteria or bacterial toxoids acting as an additional antigen such as tetanus toxoid, live or inactivated *Streptococcus equi*, live recombinant vectors expressing *S. equi* antigens, live *Rhodococcus equi*, live recombinant vectors expressing *R. equi* antigens, leptospira antigens or live recombinant vectors expressing leptospira antigens, *Clostridum difficile* toxoid, live recombinant vectors expressing *C. difficile* antigens, etc. and protozoan antigens such as *Sarcocystis neurona* or *Neospora hughesi* and the like.

The new modified live viral vaccines of this invention are not restricted to any particular method of preparation but can be made by standard methods known in the art. To prepare live, attenuated vaccines from the pathogenic virus, for instance, the tissue culture adapted, live, pathogenic EHV-1 is attenuated (rendered nonpathogenic or harmless) by methods known in the art, typically through serial passages through cell cultures. One could employ the techniques described by C. T. Rosas et al., "Equine herpesvirus type 1 modified live virus vaccines: quo vaditis?" Review, *Expert Rev. Vaccines* 5(1):119-131 (2006) that show how to generate RacH and Kentucky A (KyA) EHV-1 strains by continuous in vitro passages. Attenuation of the pathogenic EHV-1 virus may also be done by gene deletions, gene insertions or viral-producing gene mutations involving many different genes such as, for example, the IR6 (inverted repeat region 6), the gene regions encoding proteins gI, gE, gM and gG, the thymidine kinase (TK) or immediate early (IE) genes and 75 genes located in the Unique Short region (US) as well as combinations thereof (C. T. Rosas et al., id.; U.S. Pat. No. 6,225,111; U.S. Pat. No. 6,193,983; U.S. Pat. No. 5,741,696; U.S. Pat. No. 5,731,188; U.S. Pat. No. 5,674,499 and U.S. Pat. No. 5,292,653; U.S. Published Patent Application No. 2007/0166330; U.S. Published Patent Application No. 2004/0109873; U.S. Published Patent Application No. 2004/063095; U.S. Published Patent Application No. 2003/0059934 and U.S. Published Patent Application No. 2003/198650; WO 2002/009750, among others).

As the terms are used in conjunction with the present invention, a "low" pre-exposure level of herpesvirus-specific CTL precursors (i.e., the level of lymphocytes in the blood possessing lethal activity against EHV-1) before the horse is exposed to the herpesvirus means a measurement of approximately 40 or lower, preferably, lower than 20 and more preferably, less than 10 per $10^6$ PBMC (equine peripheral blood mononuclear cells). The "high" levels of post-infection, leukocyte-associated viremia (i.e., the magnitude of EHV-1 virus present in the blood of horses) refer to a comparative measurement of approximately 10-fold or more over an arbitrarily selected standard level (that is, the level of EHV-1 present in the blood of horses four days after infection with a non-neuropathogenic strain of the virus), preferably, higher than 100-fold over the standard and more preferably, greater than 1000-fold higher than the standard level of the non-neuropathogenic virus. An effective infecting amount of a neuropathogenic strain of EHV-1 refers to the amount of virus that produces a neurological infection in the horse such as, for example, $10^7$ PFU (plaque forming units) of the neuropathogenic T953 strain of EHV-1 (ORF30 $G_{2254}$), though it is contemplated that the effective infecting amount is readily titrated by routine methods taking the virulence of the virus, the weight of the horse, the age of the horse, etc. into consideration. When a given value is expressed as "approximate," "about" or similar terms, it should be understood that the variation refers to acceptable standard deviations of data in the field, for instance, ±5% of the value, within six months of the specified ages of approximately 20 (i.e., can be six months younger than age 20) or one year of age (can be six months over), or within a day less than the one week old foal described herein.

For purposes of this invention, the neuropathogenic T953 strain of EHV-1 has been deposited under the conditions mandated by 37 C.F.R. §1.808 and maintained pursuant to the Budapest Treaty in the ATCC® (American Type Culture Collection) Patent Depository, University Boulevard, Manassas, Va. 20110-2209, U.S.A. Specifically, the EHV-1 T953 sample has been deposited in the ATCC on Jun. 19, 2008 and has been assigned ATCC® Patent Deposit Designation PTA-9273.

The following examples demonstrate certain aspects of the present invention. However, it is to be understood that these examples are for illustration only and do not purport to be wholly definitive as to conditions and scope of this invention. It should be appreciated that when typical reaction or experimental conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

A further understanding of the present invention may be obtained from the examples that follow below. These working examples are intended to illustrate the invention without limiting its scope.

EXAMPLES 1-4

Materials and Methods

Experimental Animals:

The experimental sample of animals used in these studies consisted of 36 adult horse mares ranging in age from 4 to 28 years. Twenty-five of the experimental horses were Thoroughbred broodmares donated to the M. H. Gluck Equine Research Center (Department of Veterinary Science, University of Kentucky, Lexington, Ky.) by local breeding farms, while the remaining 11 mixed-breed mares were provided from the experimental horse herd maintained by the University of Kentucky's equine research farm. None of the horses had been vaccinated for EHV-1 during the year preceding their use in these studies. For experimental infection with EHV-1, the horses were kept as 3 randomly assigned groups of 12 animals/group in half-acre, grassy lots at the University's equine isolation facilities. Daily health inspections, feeding and watering, preventive health activities (e.g., fly and parasite control, hoof care, vaccinations, etc.), and handling and restraint for experimental procedures were provided by farm personnel. Antipyretic, anti-inflammatory and analgesic medications were administered, as prescribed by the IACUC-approved experimental, protocol, by the principal investigator. Veterinary services (including bladder catheterization, euthanasia, antibiotic therapy, etc.) were performed, as needed, by experienced equine practitioners from a local veterinary practice. Following completion of the experimental procedures, the 30 equine survivors of infection by EHV-1 were returned to the resident horse population of the University's equine research farm.

Virus Strains:

A live, low-passaged, abortigenic strain of EHV-1 (Ky T262) was used for intra-nasal inoculation of 12 of the experimental horses. EHV-1 strain Ky T262 was isolated from an aborted equine fetus during a large-scale outbreak of herpesviral abortion ("abortion storm") on a commercial Kentucky Thoroughbred breeding farm in 1975. Its ORF30-2254 genotype was determined by DNA sequencing using routine methods to be $A_{2254}$ (J. Nugent et al., "Analysis of equine herpesvirus type 1 strain variation reveals a point mutation of the DNA polymerase strongly associated with neuropathogenic versus non-neuropathogenic disease outbreaks," *J Virol* 80:4047-4060 (2006)).

A live, low-passaged, neuropathogenic strain of EHV-1 (Ky T953) was used for intra-nasal inoculation of 24 of the experimental horses. EHV-1 strain T953 was isolated from the blood leukocytes of an adult horse that developed quadriplegia during a multiple-case epizootic of EHV-1 myeloencephalopathy at a university equestrian center in Ohio in 2003 (R. W. Henninger et al., "Outbreak of Neurologic Disease Caused by Equine Herpesvirus-1 at a University Equestrian Center," *J Vet Intern Med* 21:157-165 (2007)). Its ORF30-2254 genotype was determined by DNA sequencing using routine methods to be $G_{2254}$ (J. Nugent et al., "Analysis of equine herpesvirus type 1 strain variation reveals a point mutation of the DNA polymerase strongly associated with neuropathogenic versus non-neuropathogenic disease outbreaks," *J Virol* 80:4047-4060 (2006)).

Both strains of EHV-1 were originally isolated in monolayers of an equine dermal fibroblast cell line and propagated at low multiplicity of infection (moi=0.1) using the same cell line for production of the virus stocks used for horse inoculation.

Inoculation of Horses with EHV-1:

Preinfection blood and nasopharyngeal samples were collected, and baseline rectal temperatures were recorded. To initiate viral infection, each horse was inoculated intra-nasally with $10^7$ plaque-forming units (PFU) of EHV-1 by use of a fenestrated, 30.5 cm (12 inch) rubber catheter. The course of infection was followed by daily monitoring of clinical signs and rectal temperatures. Nasopharyngeal secretions were collected daily for 7 days with 16-inch, flexible, rayon-tipped swabs (for example, PROCTO SWAB® commercially available from Henry Schein, Inc., Melville, N.Y.) and processed for virus isolation by inoculation of monolayers of equine dermal cells. Both coagulated and heparinized venous blood samples were collected at 2, 4, 6, 8, 10, 12, 14 and 21 days post inoculation and processed for serum and peripheral blood mononuclear cells (PBMC), respectively.

The severity of clinical neurologic signs in the EHV-1 inoculated horses was graded using a simplification of the scale described by Mayhew (I. Mayhew, "Evaluation of the large animal neurological patient," *Large Animal Neurology: A Handbook for Veterinary Clinicians* 1989, Philadelphia, ed., Lea & Febiger, pp 3-69). The observed neurologic deficits were categorized and recorded as either grade 1 (decreased tail muscle tone or toe-dragging), grade 2 (any other walking gait abnormality or bladder atony), or grade 3 (recumbency).

Preparation of DNA from Equine Peripheral Blood Mononuclear Cells (PBMC):

PBMC were purified by Ficoll-Hypaque centrifugation of heparinized venous blood samples collected from horses inoculated with EHV-1 (using, for example, Ficoll-Paque PLUS® commercially available from GE Healthcare, Piscataway, N.J.) as previously reported (G. P. Allen and C. C. Breathnach, "Quantification by real-time PCR of the magnitude and duration of leukocyte-associated viraemia in horses infected with neuropathogenic versus non-neuropathogenic strains of equine herpesvirus-1," *Equine Vet J* 38:252-257 (2006)). For each test sample, RNA-free total DNA was isolated from $5 \times 10^7$ PBMCs using a commercial kit designed for purification of genomic DNA from blood leukocytes (for example, Wizard Genomic DNA Purification Kit® commercially available from Promega, Madison, Wis.). Purified DNA was dissolved in 200 µL of sterile water and quantified via measurement of absorbance at 260 nm.

Real-Time PCR Quantification of EHV-1 DNA:

A real-time PCR assay was used for quantitative detection of EHV-1 DNA present in peripheral blood mononuclear cells of horses following experimental inoculation of EHV-1 in accordance with conventional techniques previously described (G. P. Allen and C. C. Breathnach, 2006, id). The assay was performed using TaqMan® detection chemistry (commercially available from Applied Biosystems, Foster City, Calif.) and the 7500 Real-Time PCR system (using, for example, 7500 SDS Software®, ver. 1.3.1, commercially available from Applied Biosystems, Foster City, Calif.). The real-time amplification primers and TaqMan® fluorescent detection probes used are listed in the below Table 1. For each DNA sample, triplicate real-time PCR reactions were run, each containing 1 µg of PBMC DNA in 25 µL of complete PCR reaction mixture with 900 nM primers designed to amplify a 60 bp fragment of the EHV-1 glycoprotein B (gB) gene, and 250 nM fluorescent (5'-FAM) TaqMan® probe for real-time detection of the amplified gB sequence. As an endogenous control for normalization of sample-to-sample variations in the amount of target DNA added to the reaction wells, 3 different replicates of each sample were run with the gB primer/probe set replaced with a primer pair and fluorescent probe for detection of the equine β-actin gene sequence (Table 1). Amplification parameters consisted of an initial denaturation step of 95° C. for 10 minutes followed by 45 cycles of 95° C. for 15 seconds and 60° C. for 1 minute. Quantitative comparison and statistical analysis of the results were performed by 7500 SDS Software® (ver. 1.3.1, commercially available from Applied Biosystems, Foster City, Calif.), using the Delta-Delta-$C_T$ relative quantification method for expressing observed quantitative differences in levels of EHV-1 DNA (K. J. Livak and T. D. Schmittgen, "Analysis of relative gene expression data using real-time quantitative PCR and the Delta-Delta $C_T$ method," *Methods* 25:402-408 (2001)). The quality control parameters (specificity, sensitivity, dynamic range, efficiency of amplification) and characteristics of the calibrator DNA for the real-time PCR assay have been described previously (G. P. Allen and C. C. Breathnach, 2006, supra).

TABLE 1

Real-time PCR oligo primers and fluorescent detection probes used in the study

| Primer/probe | Sequence (5' to 3') | Target DNA |
| --- | --- | --- |
| EHV1GB-JN1F | CTG CCC CTG GAG GTG TAC (SEQ ID NO: 1) | EHV-1 gB |
| EHV1GB-JN1R | TTG CGG CGC TGT ATT TCG (SEQ ID NO: 2) | EHV-1 gB |
| EHV1GB-JN1M1 | FAM-CAC CGG CCT GCT AGA CT-NFQ (SEQ ID NO: 3 with minor groove binder adduct) | EHV-1 gB |
| EQBACTINIS-JN3F | CCC CGA GGC CCT CTT C (SEQ ID NO: 4) | Equine β-actin |

TABLE 1-continued

Real-time PCR oligo primers and fluorescent detection probes used in the study

| Primer/probe | Sequence (5' to 3') | Target DNA |
|---|---|---|
| EQBACTINIS-JN3R | GA GTT GAA GGT AGT TTC GTG GAT (SEQ ID NO: 5) | Equine β-actin |
| EQBACTINIS-JN3M1 | FAM-CCC TCC UC CTG GGC ATG-NFQ (SEQ ID NO: 6 with minor groove binder adduct) | Equine β-actin |

FAM = 6-carboxyfluorescein reporter fluoroprobe;
NFQ = non-fluorescent quencher moiety Determination of CTLp Frequency:

Estimation of the frequency of EHV-1 specific CTL precursors (CTLp) present in the peripheral blood circulation of horses was done by a limiting dilution microculture system developed by O'Neill et al. (T. O'Neill et al., "Determination of equid herpesvirus 1-specific, CD8+, cytotoxic T lymphocyte precursor frequencies in ponies," *Vet Immunol & Immunopathol* 70:43-54 (1999)). Seven, two-fold dilutions of PBMC responder cells were cultured in vitro with autologous, stimulator PBMCs that expressed EHV-1 antigens. Stimulator PBMCs were generated by infection with 10 PFU of EHV-1 (Army-183 strain) per cell for 90 minutes followed by a 30-minute treatment at 37° C. with 25 µg/mL mitomycin-C to block proliferation of the stimulator cells during culture. Twenty-four, 200-µL replicates of each responder cell dilution were co-cultivated in 96-well round-bottomed microplates with 50,000 stimulator PBMC which functioned as antigen-presenting cells and feeder cells for support of single-cell clonal growth of CTLp. After 10 days of incubation at 37° C. in the presence of 10 Units of recombinant human interleukin-2 (rH-IL-2), the induction cultures were assayed for cytolytic activity against chromium-51 (Cr-51) labeled, EHV-1 (Amy-183 strain) infected lymphoblast targets (pokeweed mitogen stimulated PBMC), using standard techniques as described by O'Neill et al. (1999, id.). The amount of Cr-51 released into each culture well was determined after a 4-hour incubation with 10,000 target cells by counting 200-µL of cell free supernatant from each well in a gamma counter. Spontaneous Cr-51 release by target cells was determined in wells without responder cells, and maximal Cr-51 release was measured in wells containing 0.05% NP-40 detergent. A culture well was scored as lysis-positive if the supernatant counts per minute (cpm) of Cr-51 exceeded by >2-fold the mean spontaneous Cr-51 release. Frequencies of CTLp in the blood of each horse were calculated by using the statistical evaluation software program of Strijbosch et al. (L. W. Strijbosch et al., "Limiting dilution assays: Experimental design and statistical analysis," *J Immunol Meth* 97:133-40 (1987)). The frequencies of CTL precursors specific for EHV-1 are expressed as CTLp per million responder PBMC.

Determination of Serum Neutralizing Antibody Titer:

Measurement of EHV-1 serum neutralizing antibody (SNA) titers was performed by a standard microneutralization assay described previously (C. C. Breathnach et al., "The mucosal humoral immune response of the horse to infective challenge and vaccination with equine herpesvirus-1 antigens," *Equine Vet J* 33:651-657 (2001)).

Statistical Analysis:

Differences observed between experimental groups of horses in two categorical variables (e.g., age category and occurrence of neurologic disease or virus strain and occurrence of neurologic disease) were tested for statistical significance by analysis of 2×2 contingency tables by Fisher's exact test of independence. Significance of differences between experimental horse groups in numerical variables (e.g., viremic load or CTLp frequency) was tested by one-way analysis of variance. The significance of an observed linear relationship between two measured numerical variables (e.g., viremic load and CTLp frequency or viremic load and SNA titer) was examined by linear least squares regression analysis. Statistically significant relationships between one categorical variable (e.g., occurrence of disease) and one numerical variable (e.g., pre-exposure CTLp frequency or pre-exposure SNA titer) were established by logistic regression analysis.

Example 1

Relationship Among CTLp Frequency, EHV-1 Viremia and Development of Neurologic Disease To summarize the study design, 36 horse mares were used for all of the studies described herein. The 24 elderly horses (>20 years) were randomly assigned to either of two experimental groups of 12 horses each (groups A and B). The remaining 12, younger horses (<15 years) comprised experimental group C. All 24 animals in groups A and C were inoculated with $10^7$ PFU (plaque forming units) of a neuropathogenic strain of EHV-1 (T953). The 12 group B horses were inoculated with $10^7$ PFU of a non-neuropathogenic strain of EHV-1 (T262). Statistical comparisons of response variables (e.g., development of neurologic signs, magnitude of viremia, etc.) were made between experimental horse groups that differed in one or more predictor variables (e.g., challenge strain of EHV-1, age-category, breed, pre-exposure levels of CTLp or SNA titers, etc.).

Nine of the 24 horses inoculated with the neuropathogenic strain of EHV-1 (Ky T953) developed clinical signs of central nervous system disease. Grade 2 neurologic deficits were present in three of the horses, while the remaining six animals displayed grade 3 neurologic signs. A scatter plot graphical summarization of the relationship between the two numerical variables "post-infection viremic load" (y axis) and "pre-exposure CTLp frequency" (x axis) for the 24 EHV-1 inoculated horses is shown in FIG. 1 (open and filled circles). The nine horses that developed clinical signs of neurological disease (categorical variable) following EHV-1 challenge infection are indicated on the plot by the open circles. The differences between the two age groups of mares in their mean magnitude of EHV-1 viremia are significant at $P=\geq 0.05$ for after inoculation days 4 through 10. Because the appearance of the scatter plot indicated a fairly strong linear relationship between the individual values of the two parameters "pre-infection CTLp frequency" and "post-infection viremic load," a linear regression line (solid line) was fitted to the data points using the least squares computational method (for example, SigmaStat® 3.1 statistical analysis software commercially available from SYSTAT Software, Inc., Point Richmond, Calif.).

Figure 4:
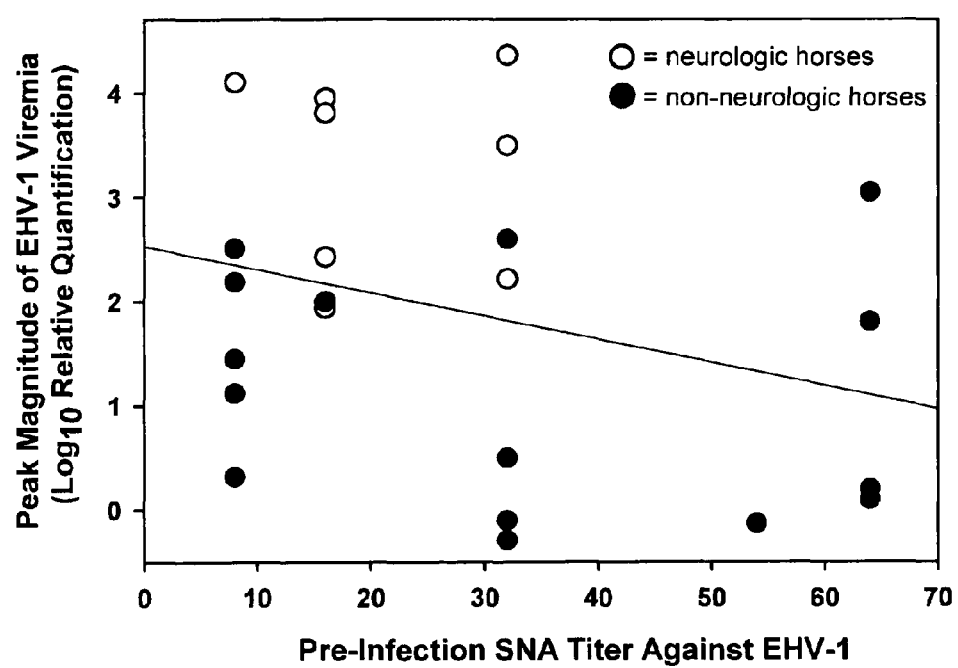
FIG. 4 illustrates the analysis of data for relationship between pre-infection serum neutralizing antibody (SNA) titer against EHV-1 and either peak magnitude of EHV-1 viremia or development of clinical neurologic disease in 24 horses following exposure to neuropathogenic EHV-1. White circles represent horses with neurologic signs while the black circles stand for the horses without neurologic signs. EHV-1 DNA present in equine peripheral blood mononuclear cells (PBMC) was quantified by real-time qPCR and the amount expressed as $\log_{10}$ of the fold-difference relative to that present in a reference calibrator PBMC DNA (relative quantification; RQ). Determination of serum levels of neutralizing antibodies specific for EHV-1 was done by a microneutralization assay. The correlation coefficient, r, between the two plotted variables is −0.31. The statistical probability (P value) that no linear relationship exists between pre-exposure SNA titer and magnitude of post-exposure EHV-1 viremia is 0.144.

The linear relationship between the two numerical values may be summarized by the slope-intercept equation, y=a+bx, where "a" is the y-intercept and the slope is represented as the number "b" value multiplied by the "x" value to obtain where the line crosses the y-axis. In terms of the present invention, "peak viremic load" (y value)=2.97 (y-intercept a value)+−0.027 (slope b value) X "pre-infection CTLp frequency" (x value). The correlation coefficient statistic r between the two numerical variables was −0.79. Simply stated, the regression line relationship can be reliably used to predict the magnitude of viremia following EHV-1 infection of a horse and its subsequent likelihood for development of neurologic signs, given the pre-infection frequency of the horses's circulating, virus-specific CTLp. Using the statistic, $r^2$, as a measure of scatter of the observed data points from the regression line, 62% of the value of the post-exposure magnitude of EHV-1 viremia in an exposed horse can be accounted for by the value of the variable "pre-exposure frequency of EHV-1 specific CTLp." The computed statistical probability (P value) that no straight-line relationship exists between the numerical values of "pre-exposure CTLp" and "post-exposure viremic load" was P=<0.001.

Of particular clinical significance was the observation that all nine horses that developed neurologic signs (open circles, FIG. 1) after inoculation with a neuropathogenic strain of EHV-1 possessed the combination of low CTLp frequency and high viremic load. Statistical significances of the observed differences in the mean viremic loads between the two age categories of horses were calculated by one way analysis of variance.

Example 2

Relationship Between Age of EHV-1 Exposed Horse and Development of Neurological Disease The association between "mare age-category" and post-inoculation development of "clinical signs of EHV-1 neurological disease" was examined. The null hypothesis was that, following inoculation of mares of different age categories with neuropathogenic EHV-1, the incidence of neurological disease would be the same in young (<15 years) and elderly (>20 years) age categories of horses.

To test the hypothesis, 12 mares belonging to each of the two age groups (<15 years or >20 years) were inoculated intranasally with $10^7$ PFU (plaque forming units) of a neuropathogenic strain of EHV-1 (T953) and observed twice daily for 3 weeks for neurologic signs. Only one mare from the <15 y age category exhibited post-inoculation neurologic signs consisting of hindlimb incoordination and dribbling of urine (grade 2) that necessitated the placement of an indwelling urinary catheter. The mare made a full recovery after 2 weeks. In contrast, 8 of the 12 EHV-1 inoculated elderly mares developed clinical signs of neurologic disease. Two of the neurologically affected old mares were ataxic only or ataxic with urinary bladder atony (grade 2), while the remaining 6 developed lateral recumbency (grade 3) and were euthanized.

Using Fisher's exact test for analysis of the experimental data, the P-value statistic was 0.009, indicating that the null hypothesis can be rejected and that there is a significantly greater risk for post-exposure development of EHV-1 neurologic signs in elderly (>20 years) horses than in horses less than 15 years of age.

The data were also analyzed for a breed effect on the development of post-infection EHV-1 neurological disease in the 24 horses. The proportion of horses that developed clinical neurological signs in the two breed categories of horses (Thoroughbred and mixed-breed mares) was not significantly different than expected from random occurrence (P=0.41).

To explore the biological basis underlying the greater susceptibility of aged (elderly) horses to EHV-1 myeloencephalopathy, the magnitude of post-inoculation cell-associated viremia that developed in the two age-categories of mares was measured and compared (FIG. 2). Statistical significances of the observed differences in the mean viremic loads between the two age categories of horses were calculated by one-way analysis of variance. The differences between the two age groups of mares in their mean magnitude of EHV-1 viremia were significant at P=≤0.05 for post-inoculation days 4 through 10. The magnitude of EHV-1 viremia was greater in the elderly category of mares at all times post-infection, with levels ranging from 10- to 200-fold higher than in the younger mares.

Example 3

Relationship Between EHV-1 Genotype and Post-Exposure Development of Equine Neurologic Disease To test the hypothesis that ORF30 $G_{2254}$ strains of EHV-1 pose a greater risk than $A_{2254}$ strains for causing EHV-1 myeloencephalopathy, 12 elderly (>20 years) mares were inoculated intranasally with $10^7$ PFU (plaque forming units) of the abortigenic T262 strain of EHV-1 (ORF30 $A_{2254}$) and 12 other elderly mares were inoculated with $10^7$ PFU of the neuropathogenic T953 strain of EHV-1 (ORF30 $G_{2254}$). All 24 of the mares possessed low pre-inoculation levels of EHV-1 specific CTLp (<40 per $10^6$ PBMC). While none of the aged horses exposed to the abortigenic strain (T262) of EHV-1 exhibited neurologic signs, 8 of the 12 elderly horses exposed to the neuropathogenic strain (T953) of the herpesvirus developed clinical neurological disease (two grade 2 and six grade 3 neurologic cases).

The virological basis for the differing levels of neuropathogenicity possessed by the two ENV-1 genotypes was explored by comparison of the magnitude of leukocyte-associated viremia exhibited by the two experimental treatment groups of horses (FIG. 3). The differences in the mean magnitude of EHV-1 viremia resulting from inoculation with the two genetic strains of EHV-1 are significant at P=≤0.05 for post inoculation days 4 through 12.

At all sampling times following virus inoculation, the circulating viremic load was significantly greater in the group of 12 horses exposed to the ORF30 $G_{2254}$ genotype (T953) of EHV-1.

Example 4

Relationship Between Pre-Exposure SNA Titer to EHV-1 and Post-Exposure Development of Equine Neurologic Disease For the 24 horses inoculated with the neuropathogenic strain of EHV-1 (T953), quantitative measurements of EHV-1 specific, serum neutralizing antibody (SNA) present at the time of virus challenge were done by microneutralization assays (FIG. 4). The correlation coefficient, r, between the two plotted variables is 0.31. The statistical probability (P value) that no linear relationship exists between pre-exposure SNA titer and magnitude of post-exposure EHV-1 viremia is 0.144. No significant association was detected between pre-exposure SNA titers and the magnitude of post-infection EHV-1 viremia. Likewise, no significant correlation between resistance of horses to EHV-1 neurological disease and pre-exposure levels of serum neutralizing antibody against the virus could be demonstrated.

Example 5

Determination of Immune Protection Against EHV-1 Neurologic Disease Using Experimental Horse Model of Present Invention Twenty-four elderly horses comprised the experimental animal study sample. Twelve horses randomly selected from the group were vaccinated by intranasal inoculation with a live, non-neuropathogenic abortion isolate of Ky T262 EHV-1. The remaining 12 horses were housed in separate facilities and sham-vaccinated by intranasal inoculation of culture medium from uninfected tissue culture cells.

Ninety days after vaccination or sham-vaccination, all 24 experimental horses were challenged by intranasal inoculation with the neuropathogenic isolate of EHV-1 (T953). The challenged horses were evaluated daily for fever, nasal discharge and neurologic dysfunction. Serum samples and PBMC were collected for 21 days post-challenge for determination of antibody titers and quantitative levels of EHV-1 viremia. As a measure of CTL activity, PBMC samples collected from each experimental horse were also analyzed for the presence of EHV-1 specific, IFN-gamma expressing cytotoxic CD8+T-lymphocytes.

The results of the vaccination-challenge study were analyzed by Fisher's exact test which identified a statistically significant reduction in the frequency of post-challenge EHV-1 neurologic disorders in the vaccinated group of horses and validated the utility of the vaccination-challenge model. Surprisingly, the live, non-neuropathogenic isolate of EHV-1 (ORF30 $A_{2254}$ genotype) was able to afford protection against EHV-1 neurologic disease. In sum, this vaccination-challenge study design finds use in the identification of live vaccine candidates that protect against neurological disease.

In the foregoing, there has been provided a detailed description of particular embodiments of the present invention for purpose of illustration and not limitation. It is to be understood that all other modifications, ramifications and equivalents obvious to those having skill in the art based on this disclosure are intended to be included within the scope of the invention as claimed.

What is claimed is:

1. An equine vaccine comprising a nontoxic, physiologically acceptable carrier and an immunogenic amount of a live, attenuated neuropathogenic strain of EHV-1 comprising the EHV-1 strain T953, wherein the neuropathogenic strain is attenuated by serial passages and the vaccine protects a horse from a neurologic form of EHV-1 disease.

2. The equine vaccine according to claim 1, further comprising an antigen selected from the group consisting of: EHV-4, EHV-5, Equine Influenza Virus, Eastern Encephalomyelitis Virus, Western Encephalomyelitis Virus, Venezuelan Encephalomyelitis Virus, West Nile Virus, African Horse Sickness Virus, tetanus toxoid, *Streptococcus equi, Rhodococcus equi*, leptospira, *Clostridum difficile, Sarcocystis neurona, Neospora hughesi*, a recombinant protein or a recombinant vector expressing a protein derived therefrom and a combination thereof.

3. The equine vaccine according to claim 1, further comprising an adjuvant.

4. The equine vaccine according to claim 3, wherein the adjuvant comprises squalane and a polyoxypropylene-polyoxyethylene block copolymer.

5. A method of protecting a horse against neurologic disease or viral infection caused by a neuropathogenic strain of EHV-1 comprising administering to the horse in need of protection an immunologically effective amount of the equine vaccine according to claim 1.

6. The method according to claim 5, which comprises administering the vaccine orally, intranasally, intramuscularly, intrarectally, transdermally or intradermally to the horse.

7. The method according to claim 5, further comprising administering an adjuvant immediately before, during or after the equine vaccine is administered or, alternatively, administering the equine vaccine further containing an adjuvant.

8. The method according to claim 7, wherein the adjuvant comprises squalane and a polyoxypropylene-polyoxyethylene block copolymer.

* * * * *